US009168301B2

(12) United States Patent
Chou et al.

(10) Patent No.: US 9,168,301 B2
(45) Date of Patent: Oct. 27, 2015

(54) USE OF BORIC ACID IN BORON NEUTRON CAPTURE THERAPY FOR LIVER CANCER (75) Inventors: Fong-In Chou, Hsinchu (TW); Sy-Yu Lin, Taipei (TW); Hong-Ming Liu, Hsinchu (TW); Jinn-Jer Peir, Hsinchu (TW); Hsiao-Ping Chung, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 321 days.

(21) Appl. No.: 13/403,168

(22) Filed: Feb. 23, 2012

(65) Prior Publication Data
US 2013/0090513 A1 Apr. 11, 2013

(30) Foreign Application Priority Data

Oct. 6, 2011 (TW) .............................. 100136365 A (51) Int. Cl.
*A61N 5/00* (2006.01)
*A61K 51/00* (2006.01)
*A61K 41/00* (2006.01)
*A61N 5/10* (2006.01)
(52) U.S. Cl.
CPC ....... *A61K 41/0095* (2013.01); *A61N 2005/109* (2013.01)

(58) Field of Classification Search
CPC ................ A61N 2005/109; A61N 2005/1098; A61N 5/10
USPC ....................................... 600/1; 128/897–899
See application file for complete search history.

(56) References Cited

U.S. PATENT DOCUMENTS 5,630,786 A * 5/1997 Griffin et al. ..................... 600/3
2012/0027873 A1* 2/2012 Schlingensiepen et al. .. 424/649

OTHER PUBLICATIONS

Rolf F. Barth, Jeffrey A. Coderre, M. Graça H. Vicente, et al. "Boron Neutron Capture Thereapy of Cancer: Current Status and Future Prospects." Clinical Cancer Research 2005; 11(11) Jun. 1, 2005.*
FI Chou, HP Chung, HM Liu, CW Chi, WY Lui. "Suitability of boron carriers for BNCT: Accumulation of boron in malignant and normal liver cells after treatment with BPA, BSH, and BA." App Rad and Isotopes 67 (2009) S105-S108.*

* cited by examiner

*Primary Examiner* — Christine H Matthews
*Assistant Examiner* — Joshua D Lannu
(74) *Attorney, Agent, or Firm* — Bacon & Thomas, PLLC (57) ABSTRACT

The present invention provides a boron drug for boron neutron capture therapy for liver cancer, which is an aqueous solution of boric acid.

16 Claims, 4 Drawing Sheets

USE OF BORIC ACID IN BORON NEUTRON CAPTURE THERAPY FOR LIVER CANCER

FIELD OF THE INVENTION

The present invention relates to a boron drug of boron neutron capture therapy (BNCT) for treating liver cancer, and particularly to a new use of using boric acid as the boron drug of BNCT for treating liver cancer.

BACKGROUND OF THE INVENTION

Using the boron neutron capture therapy (BNCT) to treat liver cancer should be a valuable method of treatment, but it also needs to have at least the following advantages: non-invasive and without the side effects from the chemical treatments, has almost no adverse effects on the normal liver cells so as to allow for quick recovery in patients, but the aforesaid requirements could not be satisfied due to the lack of adequate boron drugs in the previous methods.

Before the present invention, the use of BNCT to treat cancer was mostly based on boron drugs that result in the highest ratio of boron concentrations between a tumor and the normal tissues (T/N ratio, the higher the better), such that only the tumor cells are selectively killed during the BNCT treatment. Currently, the human clinical trials using BNCT for treating cancer include boron drugs such as BPA (Boronophenylalanine) and BSH (Borocaptate sodium).

BSH is a water-soluble boron drug, and had been approved by the FDA to be used as a boron drug in the BNCT clinical trials. BSH is commonly used in the BNCT clinical trials for treating glioma patients. When the blood-brain barrier (BBB) functions normally, BSH is unable to penetrate this barrier, but because BBB is damaged by tumors and thus became incomplete in the glioma patients, BSH is able to penetrate the barrier and into the tumor cells.

BPA is also a boron drug that had been approved by the FDA for use in the BNCT clinical trials; it is water-soluble and an analog of phenylalanine. Because the expression of amino acid transporters on the membrane of tumor cells is different from that in the normal cells, the uptake of BPA by tumor cells was usually higher than that by normal cells. However, according to the previous animal models in which BPA was used as a boron drug, the pancreas adjacent to the liver had a higher concentration of boron accumulated therein [F. I. Chou, H. P. Chung, H. M. Liu, C, W. Chi, and W. Y. Lui, "Suitability of boron carriers for BNCT: accumulation of boron in malignant and normal liver cells after treatment with BPA, BSH and BA," Applied Radiation and Isotopes vol. 67, pp, 105-108, 2009.]. Therefore, when neutron irradiation was carried out and the liver tumor had acquired sufficient treatment dose, the pancreas was severely damaged because of the neutron capture reaction. Therefore, when BPA is used as a boron drug in a BNCT clinical trial for treating a liver tumor, a patient's liver has to be removed by surgery after the injection of BPA, so as to carry out ex vivo neutron irradiation of the liver tumor. That is, the tumor-bearing liver cannot undergo neutron irradiation in vivo. But the ex vivo neutron irradiation has certain limitations and risks; for example, its success is dependent on a surgeon's organ removal technique, a patient's physical conditions, and sterilization throughout the surgery. In 2007, Suzuki and his colleagues had attempted the first case of using BNCT to treat primary liver cancer in a patient, in which BPA and BSH was injected into the liver by the hepatic artery, then BSH was mixed with lipiodol in order to carry out embolization. This method had significantly reduced the risks of the BNCT treatment process, but it failed to successfully treat the liver cancer in the patient. The patient had suffered a relapse and died of liver failure at 10 months after the BNCT treatment.

Boric acid (BA) has a molecular formula of $H_3BO_3$ and a molecular weight of 61.83 g/mol. Under normal physiological pH, it appears to be a uncharged small molecule and has a molecular volume of 71.5 $Å^3$, which is even smaller than that of uric acid (75.3 $Å^3$). Once the naturally occurring boron atoms dissolves in water, they exist as the weakly acidic boric acid. The B—O bonding in the boric acid is very stable so boric acid is nearly never metabolized in the living creatures. In addition, boric acid is widely applied in our daily lives and commonly used in pesticides, weed killers, and preservatives, thus its biological toxicity in humans, rats, and rabbits via oral intake had been thoroughly studied. In a living creature, boric acid is quickly and passively transported and diffused throughout the body and into cells along with the body fluids. In the early studies of accumulation of boron drugs in tumors and normal tissues, boric acid is frequently used as a reference compound, and previous studies had shown that boric acid has an accumulation efficiency of 1 in the cells. In the studies of cell culture, it was shown that boric acid was evenly distributed in the GS-9L, U-343MGa, HeLa, V79, and B16 cells [J. A. Coderrea and G. M. Morrisb, "The radiation biology of boron neutron capture therapy," Radiation Research, vol. 151, pp. 1-18, 1999.], [J. Capala, M. S. Makar, and J. A. Coderre, "Accumulation of boron in malignant and normal cells incubated in vitro with boronophenylalanine, mercaptoborane or boric acid," Radiation Research, vol. 146, pp. 554-60, 1996.].

After a tumor-bearing rat had been treated with the boron drug sulfhydryl borane dimer, the boron concentration in its blood was analyzed by using the Prompt-γ spectrometry, which utilizes boric acid as an internal control [D. D. Joel, R. G. Fairchild, J. A. Laissue, S. K. Saraf, J. A. Kalef-Ezra, and D. N. Slatkin, "Boron neutron capture therapy of intracerebral rat gliosarcomas," Proceedings of the National Academy of Sciences of the United States of America, vol. 87, pp. 9808-9812, 1990.].

Studies based on using the electroporation method to increase the uptake of a boron drug ($^{10}$B-BSH) in tumor cells revealed that when using boric acid as a reference for comparison, $^{10}$B-boric acid freely enters and leaves the cells, and the concentration of $^{10}$B in the cells and in the liquid culture was identical, and showed no accumulation in the cells.

According to the principle of BNCT treatment, the ratio of boron concentrations of a boron drug accumulated in the tumor and the normal tissues need to be higher than 2.5 to 3 [R. F. Barth, J. A. Coderre, M. G. H. Vicente, and T. E. Blue, "Boron neutron capture therapy of cancer: current status and future prospects," Clinical cancer research, vol. 11, pp. 3987-4002, 2005.], such that the BNCT treatment can effectively kill the tumor cells, while damage to the normal tissues can be reduced to acceptable levels. As boric acid enters and leaves the cells by simple diffusion or passive diffusion, and is not selectively accumulated, it results in a ratio of boron concentrations of 1 intracellularly and extracellularly. Because boric acid does not result in any specific accumulation effects in the soft tissues of a living creature, it does not fulfill the requirement of specific accumulation of a boron drug in a tumor that the BNCT treatment is based on, thus boric acid is mostly used as an internal reference in the BNCT studies to test the distribution of a boron drug in a living creature, or as an internal standard for analyzing the boron concentration. There have not been any BNCT treatments that use boric acid as a boron drug until now.

SUMMARY OF THE INVENTION

A primary objective of the present invention is to provide a novel boron drug for boron neutron capture therapy (BNCT) for liver cancer.

Another objective of the present invention is to provide a method for treating liver cancer by BNCT.

In order to accomplish the aforesaid objectives a novel boron drug for BNCT for liver cancer provided by the present invention is boric acid.

The present invention provides a BNCT method for treating a liver cancer in a subject, which comprises administering boric acid to said subject, and subjecting said liver cancer in the subject to neutron irradiation.

Preferably, said boric acid is in the form of an aqueous solution.

Preferably, said administering comprises intravenously injecting said aqueous solution of boric acid to said subject.

Preferably, boron of said boric acid is composed of a major portion of $^{10}B$ stable isotope. More preferably, boron of said boric acid is composed of about 99% of $^{10}B$ stable isotope.

Preferably, said subject is human.

Preferably, said administering comprises intravenously injecting said aqueous solution of boric acid to said human in a dose of about 5-60 mg of $^{10}B$ stable isotope per kilogram of human body weight. The previous study shows that an injection dose of boric acid with 60 mg of $^{10}B$ stable isotope per kilogram of human body weight has no permanent adverse effect. Accordingly, the boric acid is administered with an amount not exceeding 60 mg of $^{10}B$ stable isotope per kilogram of human body weight to avoid adverse effects, unless future study indicates otherwise.

Preferably, said liver cancer in the subject is started to be subjected to the neutron irradiation within the $10^{th}$ to the $120^{th}$ minute, and more preferably the $30^{th}$ to the $80^{th}$ minute, immediately following the intravenous injection. Preferably, said neutron irradiation is carried out with a physical dose of 5-12 Gy, and more preferably, 7-10 Gy.

Preferably, the BNCT method of the present invention further comprises measuring a concentration of $^{10}B$ stable isotope in the subject's blood, wherein said neutron irradiation is carried out when the measured concentration drops to a desired value, and preferably higher than 20-35 μg $^{10}B$ stable isotope/mL The present invention further discloses a method of using boric acid in treating a liver cancer in a patient by BNCT, which comprises preparing an aqueous solution of boric acid, wherein boron of said boric acid is composed of a major portion of $^{10}B$ stable isotope; and intravenously injecting said aqueous solution of boric acid to said patient in a dose of about 5-60 mg of $^{10}B$ stable isotope per kilogram of patient body weight within a period of the $10^{th}$ to the $120^{th}$ minute, and preferably the $30^{th}$ to the $80^{th}$ minute, prior to neutron irradiation being conducted to said patient.

The present invention still further discloses a method of using boric acid in treating a liver cancer in a patient by BNCT comprising preparing an aqueous solution of boric acid, wherein boron of said boric acid is composed of a major portion of $^{10}B$ stable isotope; intravenously injecting said aqueous solution of boric acid to said patient in a dose of about 5-60 mg of $^{10}B$ stable isotope per kilogram of patient body weight; and monitoring a concentration of $^{10}B$ stable isotope in the patient's blood to decide when neutron irradiation is conducted to said patient. Preferably, said monitoring comprises measuring concentrations of $^{10}B$ stable isotope in the patient's blood and comparing the measured concentrations to a desired value to decide when neutron irradiation is conducted to said patient, wherein said desired value is higher than 20-35 μg $^{10}B$ stable isotope/mL.

DETAILED DESCRIPTION OF PREFERRED EMBODIMENTS

The present invention made the unexpected discovery that when using an aqueous solution of $^{10}B$-boric acid as the single boron drug of BNCT for treating liver cancer, the liver tumor cells could be selectively destroyed.

The Unexpected Discovery $^{10}B$-boric acid does not result in specific accumulation in the soft tissues, which means the boron concentrations ($^{10}B$) in each of the soft tissues in a living creature are similar after $^{10}B$-boric acid administration [F. I. Chou, H. P. Chung, H. M. Liu, C. W. Chi, and W. Y. Lui, "Suitability of boron carriers for BNCT: accumulation of boron in malignant and normal liver cells after treatment with BPA, BSH and BA," Applied Radiation and Isotopes vol. 67, pp. 105-108, 2009.], and thus the boron concentrations in tumor cells and adjacent to normal cells should also be similar to each other. When the inventors of the present invention injected the liver tumor-bearing rats with $^{10}B$-boric acid in the BNCT treatment, they were surprised to find that the liver cancer in the rats had completely disappeared, and the adjacent organs like pancreases and spleens did not show radiation damage in tissue histopathological sections thereof.

Significant Improvement in the Treatment Effects:

When the FDA-approved $^{10}B$-BPA is used as a boron drug in the BNCT for treating tumors, the ratio of boron concentrations accumulated in the tumor and the adjacent to normal organs must be evaluated by using $^{18}F$-BPA Positron Emission Tomography (PET) first. In other words, if a boron drug that is similar to $^{10}$B-BPA (high T/N ratio) is developed for use in the BNCT for treating liver cancer, this step of labeling the boron drug with radioisotope (such as $^{18}$F) and evaluating the boron drug T/N ratio by PET cannot be avoided. But in the present invention, boric acid is used as a boron drug in the BNCT for treating liver cancer, which does not require the step of labeling the boron drug with radioisotope or evaluating the boron drug T/N ratio by PET. This is due to the fact that boric acid does not result in specific accumulation in the soft tissues of a living creature, so the boron concentrations in a patient's blood and in the liver tumor are approximately equal. Consequently, it is not necessary to evaluate the ratio of boron concentrations between the blood (or normal tissues) and the tumor by PET before neutron irradiation. The inventors of the invention hypothesize that boric acid is an effective boron drug in the BNCT for treating liver cancer because the normal vasculature in the liver is structurally complete, whereas the vasculature of the liver tumor is structurally incomplete and abnormal, which leads to different levels of damage between the two after the BNCT treatment; though the possible causes for this phenomenon are not limited to the above hypothesis. After doing a Doppler ultrasound examination, it was indicated that following the BNCT treatment, the distribution of blood vessels to the liver tumor gradually decreased and disappeared, which led to clear inhibition of blood flow around the tumor. In the present invention, it is only necessary to inject a patient with boric acid intravenously, and then carry out the BNCT treatment of adequate doses within the $10^{th}$ to the $120^{th}$ minute (effective period) after the injection, the liver tumor cells can then be selectively killed as a consequence. In contrast, when $^{10}$B-BPA and BSH are used as the boron drug in the BNCT for treating liver cancer, a patient needs to be administered with two boron drugs including BSH and BPA via hepatic artery catheter injection and embolization.

The present invention can be further understood by referring to the following detailed experiments, in which the experiments are meant to illustrate the preferred embodiments of the present invention, and are not meant to limit the scope of the present invention.

Experiments

Materials and Method

1. The Preparation of a Boron Drug and the Measurement of Boron Concentration

According to the present invention, the boron drug used in the BNCT for treating liver cancer is boric acid.

The Preparation of Boric acid (BA) Aqueous Solution

The molecular formula for boric acid is $H_3BO_3$, which has a molecular weight of 61.83. The boron atom of boric acid used in the experiment comprises 99% of $^{10}$B boron atoms, and 1% of $^{11}$B boron atoms (Sigma-Aldrich Co. LLC). The boric acid aqueous solution was prepared by adding an adequate amount of boric acid powder in a saline solution to attain the required $^{10}$B concentration.

The Measurement of Boron Concentration

Before measuring boron concentration of a sample, it needs to undergo microwave digestion first. A sample was initially placed into a Teflon high-pressure digestion vessel, then added with 3 mL of concentrated nitric acid (14N, 65%) and 0.5 mL of hydrogen peroxide (30-35%), and the vessel was sealed before placing the vessel into a microwave digestion system (MLS 1200 Milestone, Italia) for sample decomposition. The decomposition was achieved in two stages; the first stage of digestion proceeded for 3 minutes with power set at 300 W, and the second stage of digestion proceeded for 2 minutes with power set at 600 W. Finally, the sample was allowed to cool and depressurize for 20 minutes. The sample subsequently turned into a clear solution after complete digestion. After diluting the sample with deionized water, an Inductively Coupled Plasma Atomic Emission Spectrometer (ICP-AES, OPTIMA 2000 DV, PerkinElmer Instruments) was used to measure the boron concentration of the sample. For the conditions of the analysis, the temperature of argon plasma was set at 6000-7000 K; the analytical wavelength was set at 249.773 nm, and the liquid uptake rate was set at approximately 2 mL/min; the operating voltage after the formation of plasma was set at 40 V.

2. The Establishment of Liver Tumor-Bearing Animal Model

The liver tumor-bearing animal model for liver cancer was established by using the Sprague-Dawley (SD) rats, so as to carry out animal experiments using BNCT to treat liver cancer.

The Tumor Cell Culture

The N1-S1 rat hepatoma cell line (ATCC, CRL-1604) was used in the experiments.

The N1-S1 cells were cultured in the IMDM medium (Iscove's modified Dulbecco's medium; GIBCO) prepared by pouring IMDM powder and sodium bicarbonate ($NaHCO_3$) into a serum bottle and adding an adequate amount of deionized water thereinto, this was followed by sufficient stirring and then the addition of 2 mM L-glutamine and a mixture of 1% penicillin and streptomycin antibiotics (PS, 100 U/mL penicillin, 100 μg/mL streptomycin); the pH value of the medium was adjusted to between 7.2-7.3 by using hydrochloric acid (HCl) and sodium hydroxide (NaOH). Subsequently, the medium was added with 10% fetal bovine serum (FBS) then filtered with a 0.2 μM filtering membrane. The medium was kept in the fridge at 4° C. for later uses. N1-S1 cells were maintained in suspension culture flasks at 37° C. and 5% $CO_2$ until needed for inoculation. To maintain the culture, as the N1-S1 cells were reached a density of $1.5×10^6$ cells/mL, cells could either be suctioned along with the medium directly, and then diluted by adding a fresh medium and divided into new culture flasks, or centrifuged (1000 rpm for 5 minutes) first and then discarded the old medium, followed by adding a fresh medium before being divided into new culture flasks.

The Minor Cell Implantation

Male SD rats were the animals used for the liver tumor-bearing animal model in this invention. After purchasing, the rats were bred in cage for at least one week at temperature of 22° C. and humidity of 40-70% before carrying out the experiments. An artificial lighting condition (12 h on/12 h off) was maintained in the room. The animal feeds and water were unlimited.

The implantation of tumor cells: before anesthesia, the SD rats were subcutaneously injected with 0.1 mg/kg bw of Atropine, so as to inhibit the secretion of respiratory tract and salivary gland caused by anesthetics, and prevent bradycardia resulted from the overactivity of vagus nerve. After administering Atropine for 10-15 minutes, the rats were intraperitoneally injected with 20-40 mg/kg bw of Zoletil 50 and 10 mg/kg bw of Xylazine to anesthetize and sedate the animals. After the anesthetia, the subxiphoid incision was done to allow for tumor implantation. A surgical area on the rat was shaved and disinfected with 75% alcohol and iodine, and then a 3-cm incision was made along the midline of thin layer; the muscle layer was elevated to make an opening smaller than the skin layer, and both sides of the rat's abdomen was gently pressed to reveal the liver. A 29 G syringe was loaded with the N1-S1 tumor cell suspension in advance, and then used to slowly inject the suspension into a hepatic lobe of the rat; each of the rats were injected with $6×10^6$ cell/0.1 mL of the suspension. After the implantation, the peritoneum was stitched back with an absorbable suture, before using a nylon suture to stitch back the skin layer. The operated rats were then released back into the cage, and their activities and survival were continuously monitored.

The Monitoring of Liver Tumors with Ultrasound

A commercial ultrasound scanner (TOSHIBA Xario) was used to scan the liver tumors, and a linear probe (PLT-1204BT) was used because it imparts better resolution; the frequency of the scanning was set at 14 MHz. After the anesthesia, the experimental animals were subjected to B-mode ultrasound imaging, so as to confirm whether the induction and growth of the tumors. A normal liver approximately locates within 2 cm subcutaneously. Sagittal sections and transverse sections were obtained for the experimental animals before the BNCT treatment, and on the $10^{th}$, $30^{th}$, $60^{th}$, and $80^{th}$ day after the BNCT treatment, in order to estimate the size of the tumors, and also combined Doppler mode with 3D imaging to evaluate the distribution of vasculature in the tumors, as well as the relative position of the tumors in the abdominal cavities.

3. The Pharmacokinetic and Biodistribution Analysis of Boric Acid in Rats

The Pharmacokinetic Analysis

Boric acid was used as a boron drug to do the animal experiments; drugs were administered to the rats via their tail veins (intravenously), and the dose of the administered boric acid was 25 mg $^{10}$B/kg bw. Blood samples were drawn from the animals at adequate times before and after the administration to measure the boron concentration in the blood, in order to understand the changes in the pharmacokinetics of the boron drug. The blood was stored in heparin tubes, and the blood samples were evenly mixed with an equal amount of 2.5% Triton X-100 (a surfactant), respectively, then diluted with 1% nitric acid, which allowed the boron concentrations of the samples to be analyzed by using the inductively coupled plasma atomic emission spectroscopy (ICP-AES).

The boric acid was administered intravenously via one-shot injection, and then blood samples were drawn after an adequate period of time to analyze changes in boron concentration of the blood. The relationship between boron concentration and time was described in graphs by using a two-compartment model, which meant using the double exponential formula $C(t)=Ae^{-\alpha t}+Be^{-\beta t}$ to represent a trend line in order to understand changes in the pharmacokinetics of the boron drug. Subsequently, the WinNonlin application (version 5.3, Pharsight, Mountain View, Calif.) was used to calculate parameters thereof, wherein the parameters included the concentration of the drug in the central chamber (A), the concentration of the drug in the tissues (B), the half life of the drug distribution (Alpha-HL), the half life of the drug excretion (Beta-HL), the highest drug concentration in blood ($C_{max}$), the area under curve (AUC) showing drug concentration in blood versus time, the distribution volume of the drug in the rats when it has become stabilized ($V_{ss}$), the half life for the drug when it has been excreted from the central chamber ($K_{10}$-HL), the mean residence time (MRT), and the clearance rate (CL) of the drug.

The Biodistribution Analysis of the Boron Drug

Boric acid was administered to the rats via their tail veins, and then the liver tumor-bearing rats were sacrificed at 30 minutes, 1 hour, 2 hour, and 4 hour after the drug administration, in which an average diameter of the tumors was approximately 1-1.5 cm. The central portions and the peripheral of the tumor, the normal liver tissue on the tumored lobe, the normal liver tissue on the normal lobe, the lung, the kidney, the heart, the intestine, the pancreas, the spleen, the stomach, the testis, and the muscle tissue were collected, and then frozen at −20° C. for analysis of boron concentrations in the tissues.

The Analysis of Boron Concentration

Before carrying out the analysis of boron concentration for the tissue samples, the samples must first be digested. The samples were weighed before the digestion, and the weight of a sample had to be larger than 0.2 g, and was preferably 0.5 g. The samples underwent microwave digestion as described above. The resulted solutions were confirmed to be completely dissolved once they had become clear in appearance, and the solutions were obtained and diluted by adding deionized water thereinto, then had boron concentrations thereof analyzed by using ICP-AES.

4. The BNCT Treatment

The Design of Neutron Irradiation Fixture for Irradiating Liver Tumors in Rats and Calculation of Doses Thereof For the purpose of irradiating a rat's abdominal regions, a collimator for performing neutron irradiation in a liver tumor-bearing rat was designed as having two symmetrical circular recesses with 2 cm in diameter, and it allows two rats to be irradiated simultaneously. The Monte Carlo N-Particle transport code system (MCNP) and a verified neutron source file thereof were used to simulate and calculate the neutron flux from an outlet of the beam aperture through different materials and thickness on a living creature, so as to optimize the irradiation conditions. The fixing frames consisted of polymethylmethacrylate (PMMA) and the collimator consisted of polyethylene (PE). For a reference about the parameters of the composition of different materials and the rats, the material composition report from the NIST (National Institute of Standards and Technology) and the $46^{th}$ report from the ICRU (International Commission on Radiation Units and Measurements) were referred to, and volumes and positions of the organs were specified by using mathematical formulas based on the sizes of the real organs. Finally, simulations were performed so as to determine an irradiation time for each of the rats. In addition, a maximum allowable dose for each of the organs might be estimated by utilizing the boron concentrations of the tissues, the relative biological effectiveness (RBE) of neutrons for the tissues, and comparisons of the acceptable doses for normal organs during the traditional radiation treatments. Using the maximum allowable dose of the normal tissues adjacent to the tumor as the prescription dose for the tumor, a neutron fluence required for the irradiation was estimated after the prescription dose was determined.

The Establishment of a Neutron Irradiation Mode for Irradiating Liver Tumors in Animals The experimental animals were divided into three groups; a normal group (which was made up of normal rats), a tumor comparison group (in which the rats received the implantation of tumor cells but not the BNCT treatment), and a BNCT treatment group; the BNCT treatment group was divided into subgroups of rats that received different physical doses of irradiation.

The rats implanted with the N1-S1 tumor cells were subjected to the BNCT treatment on the $17^{th}$ day after the implantation. The BNCT irradiation was performed at the point when boric acid had reached the optimal distribution in a rat's body and a tumor, with reference to the aforesaid experimental results of drug administration in rats. The rats were temporarily anesthetized by gas anesthesia, and then intravenously injected with boric acid of 25 mg $^{10}$B/kg bw. At 15 minutes before the irradiation, the rats were injected with Atropine and Zoletil to allow for longer anesthesia. Each of the rats were placed on a fixing frame with its tumor-bearing area close to the beam aperture of the Tsing Hua Open-pool Reactor (THOR), and then different duration of neutron irradiation was performed under a specific neutron flux, in order to acquire a specific irradiation dose. After the irradiation, an on-line neutron monitoring system for the THOR was used to confirm the actual irradiation dose.

5. The Evaluation of the BNCT Treatment Effects

Ultrasound Examination

The tumor was scanned by using a commercial ultrasound scanner (TOSHIBA Xario), and the scanning frequency was set at 14 MHz. A normal liver approximately locates within 2 cm subcutaneously. Ultrasound imaging was used to track growths or disappearances of the tumors, as well as changes in the blood vessels surrounding the tumors within 80 days of the BNCT treatment. The 2D mode of ultrasound imaging was employed to confirm the status of a tumor, and sagittal and transverse sections were obtained to estimate the size of the tumor, and the Doppler mode was combined with 3D imaging to evaluate the distribution of vasculature in the tumor, as well as in surroundings thereof.

The Measurement of Biochemical Parameters in the Serum

The serum biochemical parameters of the rats were monitored by drawing blood samples from the rats' tail veins once before the tumor implantation, and weekly after the tumor implantation. When a rat was sacrificed, a blood sample was also drawn from its heart. Whole blood was collected from a rat and held in a serum separation tube (Vacationer, Franklin Lakes, N.J., USA), then centrifuged for 15 minutes at 3000 rpm, followed by preserving the serum upper clean solution by freezing. Afterwards, the College of Veterinary Medicine of National Chung Hsing University was commissioned with the task of analyzing the serum biochemical parameters of this solution, in which a serum biochemical analyzer (Chiron Diagnostics Corporation, Oberlin, Ohio, USA) was utilized to analyze concentrations of the serum enzymes related to liver and kidney functions.

Statistical Analyses

The data values were shown as Mean±SD (mean±standard deviation). The data of the experimental groups were compared by using Student's t-test, in which a p-value less than 0.05 indicates the presence of significant differences.

Results

1. The Biodistribution of Boric Acid in Rats

The Pharmacokinetics of Boric Acid

Figure 1:
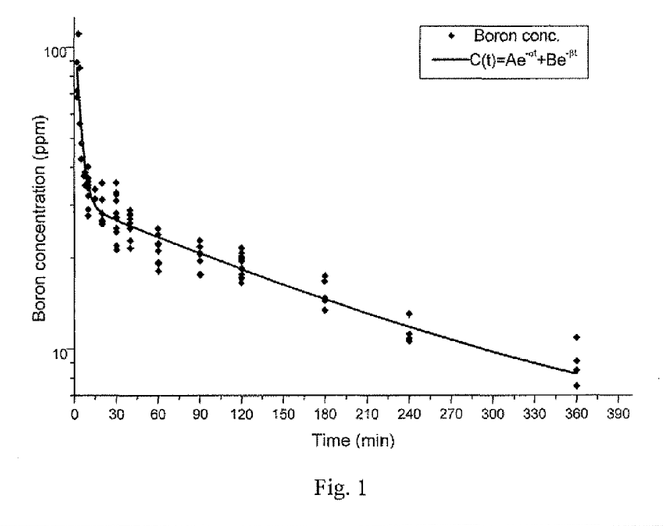
FIG. 1 shows the blood boron concentration in rats at different time intervals after the injection of boric acid, wherein the formula for the trend line is: $C(t)=Ae^{-\alpha t}+Be^{-\beta t}$

A liver tumor-bearing rat was intravenously injected with boric acid (25 mg B/kg bw) by its tail. A blood sample was drawn from its tail vein to allow for the analysis of blood boron concentration at the $5^{th}$, $10^{th}$, $20^{th}$, $30^{th}$, $40^{th}$, $60^{th}$, $120^{th}$, $180^{th}$, $240^{th}$, and $360^{th}$ minute after the injection. FIG. 1 shows the changes of blood boron concentration in the rats at different times after the injection of boric acid.

After intravenously injected a liver tumor-bearing SD rat with 25 mg B/kg bw of boric acid, a semi-log plot was used to draw a graph to show the relationship between the average blood boron concentration versus time. The data values were used to draw a trend line based on the two-compartment model formula: $C(t)=Ae^{-\alpha t}+Be^{-\beta t}$ [J. A. Jansen, J. Andersen, and J. S. Schou, "Boric acid single dose pharmacokinetics after intravenous administration to man," Archives of Toxicology, vol. 55, pp. 64-67, 1984.] The curve of the pharmacokinetics could be divided into two parts, in which one shows the sudden-drop zone within 20 minutes of the injection, and the slow-drop zone thereafter. The boric acid was metabolized according to the double exponential curve, and the two zones represent the fast distribution phase and the slow excretion phase.

The initial blood boron concentration was 104.6±36.23 μg/mL, and quickly dropped to 27.84±8.09 μg/mL within 20 minutes, then steadily decreased thereafter; it dropped to 8.3±2.57 μg/mL at 360 minutes after the injection. The α-HL and β-HL were 3.59±1.64 minutes and 232.13±100.59 minutes, respectively. Table 1 shows the average parameters of the pharmacokinetics for boric acid under one-shot injection.

TABLE 1

The pharmacokinetic parameters from an one-shot intravenous injection of boric acid as evaluated by using WinNonlin

| Parameters | Mean ± SD | Parameters | Mean ± SD |
|---|---|---|---|
| A (ppm) | 73.29 ± 35.4 | $V_{SS}$ (L) | 3.3 ± 0.99 |
| B (ppm) | 27.84 ± 8.09 | MRT (min) | 288.09 ± 108.13 |
| α-HL (min) | 3.59 ± 1.64 | CL (L/min) | 0.01 ± 0.01 |
| β-HL (min) | 232.13 ± 100.59 | $K_{10}$-HL (min) | 68.04 ± 31.8 |
| AUC (min · ppm) | 9756.30 ± 2433.34 | $K_{12}$-HL (min) | 0.16 ± 0.09 |
| $C_{max}$ (ppm) | 104.6 ± 36.23 | $K_{21}$-HL (min) | 0.06 ± 0.02 |

The values of the parameters are shown as Mean ± SD (n = 12).

The area under curve (AUC) for blood boron drug concentration versus time was 9756.30±2433.34 min·ppm. Therefore, the half life for which the drug was excreted from the central chamber ($K_{10}$-HL) was 68.04±31.8 minutes, and the rate constant ($K_{12}$-HL) for how fast the drug moves from the central chamber to the tissues was 0.16±0.09 minutes; the rate constant ($K_{21}$-HL) for how fast the drug moves from the tissues to the central chamber was 06±0.02 minutes. In addition, the clearance rate (CL) of boric acid was 0.01±0.01 L/min, and the mean residence time (MRT) of boric acid was 288.09±108.13 minutes.

The Biodistribution of Boric Acid

After injecting each of the liver tumor-bearing rats with 25 mg B/kg bw of boric acid via tail vein thereof, the rat was sacrificed at 30 minutes, 1 hour, 2 hours, and 4 hours after the injection, and the tumor and the normal tissues of liver, lung, heart, spleen, pancreas, kidney, stomach, intestine, testis, muscle, and blood were collected, in order to analyze the boron concentration remaining in these organs and tissues. The tumor was further divided into two areas including the central and peripheral portions of the tumor.

Within the period of two hours after the intravenous injection of boric acid, the boron concentration inside the liver tumors was higher than that of the normal liver, and the difference in the boron concentrations between the tumor and normal portions of liver was 20%. The boron concentration in the peripheral portions of the liver tumors were slightly higher than that of the central tissues. The difference between the boron concentrations in the tumors and the normal liver cells was insignificant at 4 hours after the injection.

Table 2 shows the measured boron concentrations in the tumors and the normal tissues at different time intervals after the drug administration. At 30 minutes after injecting boric acid, the ratio of boron concentrations between the tumors and the normal livers, hearts, lungs, pancreases, and stomachs reached approximately 1.2. Apart from the kidneys, the boron concentration in the other normal tissues was less than the boron concentration in the tumor tissues. Moreover, the boron concentration in the soft tissues reached the highest point at 30 minutes after the injection and then began to gradually decrease thereafter, except for the testes. Boron concentration in the testes slowly accumulated within 2 hours after the injection, and gradually increased over time, but began to decrease at 4 hours after the injection.

TABLE 2

The biodistribution of boric acid in a rat at different time intervals after administration.

| | Time after administration | | | |
|---|---|---|---|---|
| Organs | 0.5 h (n = 7) | 1 h (n = 5) | 2 h (n = 5) | 4 h (n = 2) |
| Tumor (center) | 25.11 ± 4.40 | 20.47 ± 0.99 | 18.57 ± 4.03 | 10.95 ± 0.70 |
| Tumor (peripheral) | 25.97 ± 4.28 | 21.03 ± 2.46 | 19.15 ± 3.83 | 10.25 ± 1.22 |
| Lobe with tumor from a normal liver | 23.11 ± 3.19 | 19.11 ± 1.02 | 17.98 ± 3.79 | 10.54 ± 1.78 |
| Normal lobe from a normal liver | 21.24 ± 4.07 | 18.82 ± 0.68 | 17.53 ± 4.51 | 10.58 ± 1.19 |
| Lungs | 22.78 ± 2.61 | 18.5 ± 1.95 | 17.539 ± 3.35 | 11.60 ± 3.08 |
| Hearts | 22.83 ± 0.62 | 17.78 ± 0.45 | 18.75 ± 2.95 | 11.08 ± 1.29 |

TABLE 2-continued

The biodistribution of boric acid in a rat at different time intervals after administration.

| | Time after administration | | | |
|---|---|---|---|---|
| Organs | 0.5 h (n = 7) | 1 h (n = 5) | 2 h (n = 5) | 4 h (n = 2) |
| Spleens | 22.72 ± 3.32 | 20.25 ± 2.72 | 18.80 ± 3.31 | 12.60 ± 4.05 |
| Pancreas | 19.92 ± 2.48 | 15.97 ± 0.97 | 14.55 ± 2.85 | 8.29 ± 0.74 |
| Kidneys | 42.36 ± 8.54 | 35.32 ± 9.61 | 24.90 ± 5.28 | 16.81 ± 1.00 |
| Stomachs | 20.55 ± 2.91 | 20.06 ± 4.76 | 17.29 ± 2.95 | 10.40 ± 0.69 |
| Intestines | 23.88 ± 3.41 | 18.90 ± 2.71 | 17.35 ± 2.80 | 9.94 ± 0.41 |
| Testes | 15.48 ± 3.41 | 16.04 ± 4.86 | 17.83 ± 0.86 | 11.77 ± 0.61 |
| Muscles | 22.76 ± 3.44 | 20.76 ± 3.96 | 16.81 ± 4.42 | 10.26 ± 0.37 |
| Blood | 23.83 ± 2.96 | 19.83 ± 1.48 | 17.98 ± 2.77 | 12.57 ± 3.47 |

The data values are shown as Mean ± SD (unit: mg B/kg).

Even though boric acid does not show specific accumulation in the soft tissues, the boron concentration in the tumor areas was found to be slightly higher than that of the other organs after the injection. At 0.5 hour, 1 hour, 2 hours, and 4 hours after the injection, the average boron concentrations in the tumors were 25.54±4.12, 20.75±1.76, 18.86±3.72, and 10.72±1.64 mg B/kg; the average boron concentrations in the livers were 22.18±3.53, 18.97±0.79, 17.76±3.93, and 10.56±1.23 mg B/kg, and the average boron concentrations in the blood were 23.83±2.96, 19.83±1.48, 17.98±2.77, and 12.57±3.47 mg B/kg.

2. The Physical Dose of Each Organ

Before the neutron irradiation, each of the liver tumor-bearing rats was injected with 25 mg B/kg of boric acid via tail veins thereof. At 30 minutes after the injection, two of the rats were placed behind the collimator, with their liver tumors aligned with the aperture of the collimator, and then underwent irradiation at different time intervals at 1.5 MW, so that the rats were received different doses of radiation.

Before the BNCT treatment, the MCNP code was used to calculate the designated physical doses for the tumor, and also for the organs surrounding the liver tumor, which were regarded as the organs at risk and included the normal liver, the mid section of the spine, the intestine, the kidney, and the testis. The physical doses received by different organs in the BNCT treatment groups were divided into 3 subgroups of doses including G1, G2, and G3. The tumors from the 01 subgroup would receive a dose of 11.18 Gy, while that from the G2 subgroup would receive a dose of 7.97 Gy, and that from the G3 subgroup would receive a dose of 5.61 Gy; the relevant dose compositions are shown in Table 3.

TABLE 3

The physical dose composition from the tissues of different BNCT treatment groups of rat with liver tumors.*

| | G1 physical dose (Gy) | | | | G2 physical dose (Gy) | | | | G3 physical dose (Gy) | | | |
|---|---|---|---|---|---|---|---|---|---|---|---|---|
| Organs | Neutron | γ | B | Total | Neutron | γ | B | Total | Neutron | γ | B | Total |
| Rat body | 0.41 | 2.16 | 2.36 | 4.93 | 0.29 | 1.52 | 1.69 | 3.50 | 0.2 | 1.05 | 1.15 | 2.39 |
| Mid-spine | 0.24 | 1.60 | 2.12 | 3.96 | 0.15 | 1.13 | 1.48 | 2.76 | 0.12 | 0.77 | 0.96 | 1.85 |
| Tumor | 1.3 | 3.84 | 6.03 | 11.18 | 0.90 | 2.68 | 4.38 | 7.97 | 0.63 | 1.86 | 3.12 | 5.61 |
| Normal liver | 1.3 | 3.84 | 5.58 | 10.72 | 0.90 | 2.68 | 4.04 | 7.62 | 0.63 | 1.86 | 2.97 | 5.46 |
| Intestines | 0.63 | 3.27 | 3.76 | 7.66 | 0.46 | 2.33 | 2.72 | 5.51 | 0.31 | 1.59 | 1.95 | 3.85 |
| Kidneys | 0.32 | 1.86 | 2.16 | 4.34 | 0.22 | 1.31 | 1.51 | 3.03 | 0.15 | 0.90 | 1.12 | 2.17 |
| Testes | 0.56 | 3.29 | 3.03 | 6.89 | 0.38 | 2.22 | 2.06 | 4.66 | 0.27 | 1.60 | 1.45 | 3.32 |

*The physical doses received by each of the tissues and organs were obtained by MCNP simulations. For a reference about the elemental composition of different substances, the reports from NIST and ICRU were referred to. The volumes and positions of the organs were specified by using mathematical formulas based on the sizes of the real organs.

3. The Evaluation of the Treatment Effects from Using Boric Acid in BNCT for Treating Liver Tumors After keeping the SD rats for one week for them to settle down, the rats were subjected to laparatomy to implant the tumor cells in liver. The rats showed slight weight loss after the surgery, but their weights steadily rose after recovering for 1-2 days. At 17 days after the tumor implantation, the size of the tumor was checked by ultrasound scanning, then subjected to BNCT treatment in THOR on the next day.

Changes in the Rats' Body Weights

Figure 2:
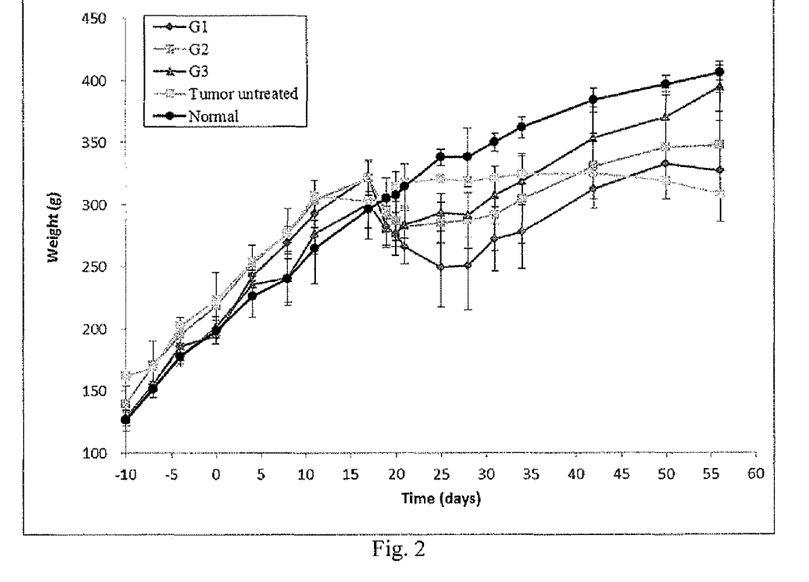
FIG. 2 shows the changes in body weight for each group of rats, after the liver tumor-bearing rats received BNCT irradiation.

The experimental rats were divided into a normal group, which was made up of normal rats without treatments; a tumor comparison group, in which the rats received the implantation of tumor cells but without BNCT treatment, and a BNCT treatment group that received three different physical doses of irradiation. The rats that received the BNCT treatment showed clear weight losses in the 3-10 days after receiving the treatment, as compared with before the treatment. But the rats from the different subgroups had their weights dropped to the lowest points at different periods of time. The rat of G1 subgroup dropped to the lowest point in weight at 8 days after the irradiation, and their weights were 78% of the initial weights; the rats of G2 subgroup dropped to the lowest point in weight at 4 days after the irradiation, and their weights were 89% of the initial weights, and the rats of G3 subgroup dropped to the lowest point in weight at 3 days after the irradiation, and their weights were 92% of the initial weights. The rats also showed slight diarrhea and appetite loss, but the rats of the lower-dose subgroups showed faster weight recovery, and the BNCT treatment subgroups of rats all showed gradual weight recovery after reaching the lowest point in weight. At about 15 days after the BNCT treatment (equal to 32 days after the implantation of tumor cells), the liver tumor-bearing rats without the BNCT treatment showed slower weight increase and their weights began to decrease at around 50 days after the tumor implantation. FIG. 2 shows the weight changes in rats of all groups; the result indicated that the weight loss after the irradiation was a temporary side effect of BNCT, and the weight could recover afterwards.

Changes in Tumor Size

The rats' tumors were checked by ultrasound scanning to show any changes in the size. It showed that at the 11$^{th}$ day after the BNCT treatment, the tumors in the three subgroups of rats from G1 to G3 had shrunk in size as compared to the size before the treatment, and the degrees of shrinkage were similar among the three subgroups. At one month after the BNCT treatment, the tumor sizes in the three subgroups of rats were less than or equal to 22% of the original tumor sizes (the smallest tumor was only 6% of the original size). The changes in tumor sizes gradually slowed down after one to two months after the BNCT treatment, and continuous tracking of the tumors until up to 80 days after the BNCT treatment did not reveal any new growth or recurrence of the tumors. In contrast, the tumor sizes in the tumor comparison group of rats had increased to 1.34 fold of the original sizes.

The Distribution of Tumor Blood Flow in Rats

In the experiments, ultrasound scanning was used to detect the distribution of tumor blood flow in rats after the BNCT treatment. 3D Doppler imaging revealed that this liver tumor had extensive vasculature. In the experiments, color Doppler ultrasound examination was employed to compare the blood flow of a tumor from 1 day before the BNCT treatment, and at the 8$^{th}$, 12$^{th}$, and 18$^{th}$ day after the BNCT treatment. The Doppler imaging for G1, G2 and G3 subgroups of the BNCT treatment groups showed that after the BNCT treatment, the distribution of blood flow surrounding the tumor gradually decreased until it could no longer be detected. This was especially significant on the 8$^{th}$ day after the treatment, as the decrease in the distribution of blood flow was the most pronounced. The decrease in the distribution of blood flow surrounding the tumor continued to decrease thereafter, but not as significant as that on the 8$^{th}$ day. However, the relationship between the decrease in the tumor blood flow and the BNCT treatment dose received thereof was not obvious, and it was deduced that the doses designated for the three subgroups had all delivered irreparable damage to the blood vessels. Although the blood flow surrounding the tumor was clearly inhibited, the blood flow of the abdominal aorta below the tumor was not affected, thus it was deduced that the larger blood vessels outside the tumor was not damaged after receiving the dose, which might be due to structural differences

TABLE 4

The shrinkage ratios in the rats' tumors detected from ultrasound scanning before and within 80 days after the BNCT treatment.

| | 1 day before BNCT | 11 days after BNCT | 30 days after BNCT | 60 days after BNCT | 80 days after BNCT |
|---|---|---|---|---|---|
| Comparison group | 0 | −0.55 ± 0.25 | −0.22 ± 0.35 | −0.48 ± 0.17 | −1.34 ± 1.26 |
| G1 | 0 | 0.64 ± 0.07 | 0.94 ± 0.01 | 0.94 ± 0.02 | 0.95 ± 0.02 |
| G2 | 0 | 0.62 ± 0.1 | 0.89 ± 0.05 | 0.86 ± 0.07 | 0.91 ± 0.05 |
| G3 | 0 | 0.48 ± 0.42 | 0.77 ± 0.06 | 0.83 ± 0.08 | 0.87 ± 0.04 |

Table 4 shows the shrinkage ratios in the rats' tumors compared between before and within 80 days after the BNCT treatment, the liver tumor-bearing rats were checked with ultrasound scanning, and then the tumor sizes were shown as ratios. The tumor ratios were calculated using the following equation [M. Feng Wu, PhD, M. Zhi-Biao Wang, PhD, M. Wen-Zhi Chen, M. Jian-Zhong Zou, M. Jin Bai, M. Hui Zhu, M. Ke-Quan Li, M. Cheng-Bing Jin, M. Fang-Lin Xie, and M. Hai-Bing Su, "Advanced hepatocellular carcinoma:treatment with high-intensity focused ultrasound ablation combined with transcatheter arterial embolization," Radiology vol. 235, pp. 659-667, 2005.]:

$$x = \frac{(A \times B) - (A' \times B')}{(A \times B)} \times 100\%$$

in which A and B in the equation represent the major axes of a sagittal section and a transverse section from scanning taken 1 day before the BNCT treatment, and A' and B' in the equation represent the major axes of a sagittal section and a transverse section from scanning taken at specific time intervals after the BNCT treatment. Zero indicates the initial size of a tumor; a negative value indicates an increase in the tumor size, and a positive value indicates a decrease in the tumor size. 1 indicates the tumor has completely vanished and is the ultimate target.

between the vessels of normal liver tissue and those of liver metastases. In comparison, the Doppler images for the tumor comparison group of rats indicated that the distribution of blood flow surrounding the tumor gradually increased over time.

The Biochemistry Analysis

The liver tumor was tracked by continuously collecting serum biochemical parameters before and after the BNCT treatment, which included GOT, GPT and BUN values. Table 5 shows the changes in the rats' GOT, GPT and BUN values before and after the BNCT treatment, and the differences between different groups of rats were displayed in the table.

Before the injection of the tumor cells, the serum biochemical parameters for all the groups were within the normal boundary. The experimental result revealed that the liver enzyme GOT clearly increased after the implantation of the tumor cells, but decreased rapidly after the BNCT treatment in all three subgroups of the BNCT treatment group that received different doses. GPT also increased after the injection of the tumor cells, but returned to normal after the BNCT treatment. In the experiments, the animals' kidney function were tracked by monitoring changes in the BUN values, in which the normal group and the BNCT treatment group did not show any meaningful changes in BUN at the time of one month after the BNCT treatment, but the tumor comparison group showed clear increase in BUN at 47 days after the implantation of the tumor cells. As the BUN values increased, the rats also showed symptoms like paralysis of the hind limbs and swollen kidneys, so it was deduced that the increase in BUN was related to the oppression of nerves and bladder by the enlarged tumor.

TABLE 5

The biochemistry analysis in rats before and within 80 days after the BNCT treatment.

| Time (day) | Normal group | Tumor Comparison group | BNCT Treatment groups | | |
|---|---|---|---|---|---|
| | | | G1 | G2 | G3 |
| GOT (AST, 83-118 U/L) | | | | | |
| −1 | 118 ± 56 | 250 ± 130 | 250 ± 148 | 271 ± 39 | 168 ± 19 |
| 11 | 106 ± 40 | 319 ± 76 | 202 ± 127 | 204 ± 9 | 180 ± 8 |
| 30 | 106 ± 26 | 419 ± 316 | 111 ± 29 | 144 ± 20 | 153 ± 3 |
| 80 | 97 ± 12 | 539 ± 128 | 127 ± 8 | 116 ± 8 | 133 ± 41 |
| GPT (ALT, 35-47 U/L) | | | | | |
| −1 | 37 ± 6 | 54 ± 8 | 54 ± 7 | 56 ± 9 | 50 ± 10 |
| 11 | 43 ± 1 | 60 ± 9 | 39 ± 13 | 45 ± 15 | 53 ± 4 |
| 30 | 49 ± 12 | 66 ± 13 | 50 ± 5 | 57 ± 3 | 55 ± 6 |
| 80 | 45 ± 1 | 61 ± 14 | 54 ± 4 | 62 ± 13 | 58 ± 12 |
| BUN (11-17 mg/dL) | | | | | |
| −1 | 14 ± 3 | 16 ± 2 | 16 ± 2 | 12 ± 1 | 13 ± 1 |
| 11 | 16 ± 2 | 16 ± 2 | 15 ± 7 | 13 ± 2 | 15 ± 3 |
| 30 | 18 ± 4 | 22 ± 6 | 14 ± 1 | 17 ± 5 | 14 ± 3 |
| 80 | 14 ± 3 | 20 ± 1 | 17 ± 3 | 16 ± 2 | 18 ± 3 |

The Histopathological Changes
4 Days after the BNCT Treatment

When observing the tumor cells on histopathological section under a microscope at low magnification, the ones from the tumor comparison group were more tightly arranged than that of the BNCT treatment group, and the tumor cells that had undergone the BNCT treatment were more loosely arranged, while there was no difference between the normal liver cells from the two groups. When studying said cells under a microscope at high magnification, it was found that the tumor cells with BNCT treatment had shrunk in size, become hollow, broken down and dead; the vicinity of tumor blood vessels was seen to be filled with fibers and connective tissues.

30 Days after the BNCT Treatment

There were no visible differences found between the subgroups of the BNCT treatment group; the tumors had generally turned into small white spots to the naked eyes, and did not show any visible differences in the histopathological sections. Therefore, the discussion about the histopathological sections obtained at 30 days after the BNCT treatment did not separately describe the subgroups of the BNCT treatment group. After the BNCT treatment, the liver tumor was independently located in the left liver lobe and did not spread to the other lobes; the tumor had clearly shrunk and appeared to be a small white spot. The histopathological sections of the tumor showed that there were independent and mid degree of fibrosis inside the white spot, along with calcification. Mononucleoside compound were also observed therein, and there were many vacuoles inside the cells. No living tumor cells were found in the sections. In addition, the liver fibrosis was found and the hemoferrin was contained, which indicated that the liver tissue was repairing itself.

The tumor in the tumor comparison group was seen to be enlarged and showed vigorous mitosis, and the cells were pleomorphic, the normal liver tissue was squeezed by the tumor.

80 Days after the BNCT Treatment

Figure 3:
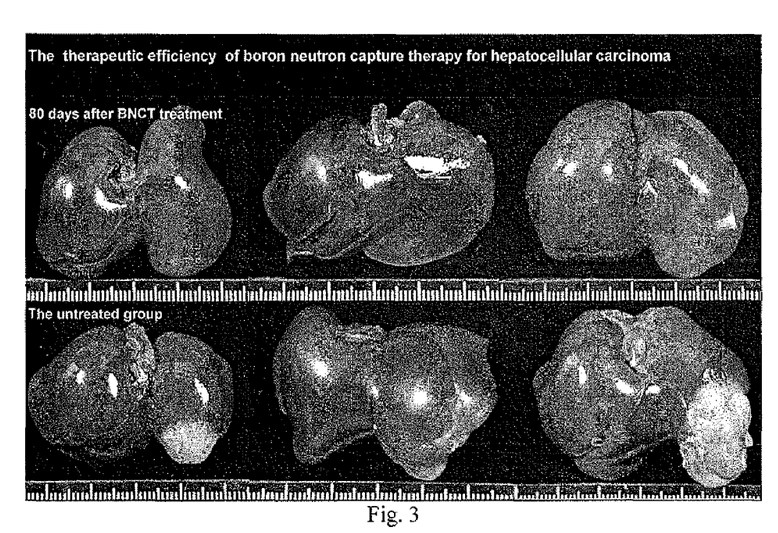
FIG. 3 shows the appearance of liver in a tumor-bearing rat on the $80^{th}$ day after receiving BNCT treatment at the upper part thereof; and the appearance of liver in a rat from the tumor comparison group without the BNCT treatment at the lower part thereof.
Figure 4:
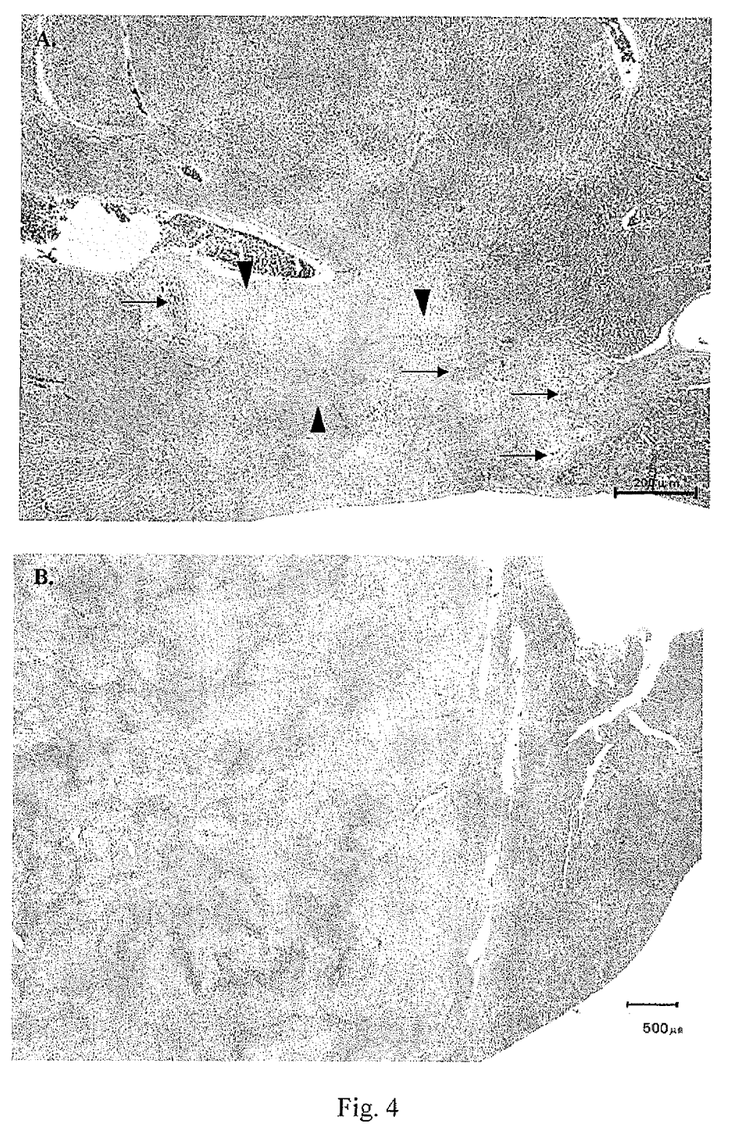
FIG. 4 show a rat's histopathological sections on the $80^{th}$ day with or without BNCT treatment, in which (A) is the histopathological section of a liver tumor after receiving BNCT treatment, and shows high level of fibrosis (the area surrounded by arrows) along with fillings by coarse calcium particles (pointed out by the arrows), no living tumor cells were observed therein; (B) is the histopathological section from a rat of the tumor comparison group wherein the tumors were not treated by BNCT, and the left part shows the liver tumor area, wherein the tumor cells away from the blood vessel appear to be dead due to excessive growth of the tumor, while the tumor cells in the nutrient-rich area grow vigorously; the rightmost part shows the area of normal liver cells.

At 80 days after the BNCT treatment, there were no differences observed between the subgroups of the BNCT treatment group, and the lesion locations were no longer visible on the tumor surface to the naked eyes (but still visible under ultrasound scanning, which appeared to be a hyperechoic spot in the liver). Therefore, the discussion about the histopathological sections obtained at 80 days after the BNCT treatment did not separately describe the subgroups of the BNCT treatment group. The upper part of FIG. 3 shows three photographs of liver from the BNCT treatment group at 80 days after the treatment, and the lower part of FIG. 3 shows three photographs of liver from the tumor comparison group obtained at the same time. The upper photographs of FIG. 3 show that there were no visible lesions on the liver surface from the BNCT treatment group. The lower photographs of FIG. 3 show that there was a lump of tumor greater than 1 cm on the right liver lobe from the tumor comparison group. FIG. 4A is a histopathological section from a rat obtained at 80 days after the BNCT treatment, in which a spot was revealed by ultrasound scanning, and shown to have mid degree of fibrosis and calcification therein, but no living tumor cells were found in the sections. FIG. 4B is a histopathological section from a rat of the tumor comparison group, which shows a large lump of tumor. The left side of FIG. 4B shows the liver tumor area, while the right side shows the normal liver cells area.

Figure 5:
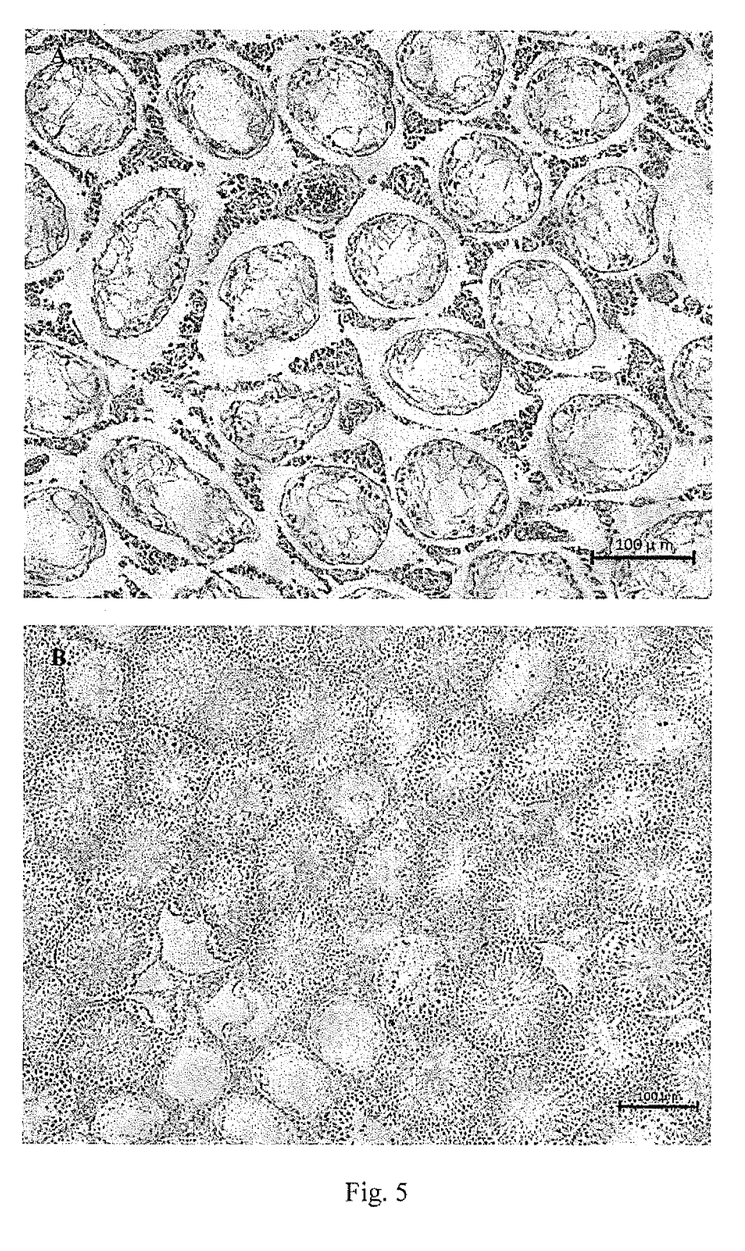
FIG. 5 show the radiation effect in the testis of a rat one month after its liver tumor was treated by BNCT, wherein (A) shows the testis from the treatment subgroup G1, which is seriously atrophied; (B) shows the testis from the treatment subgroup G3, in which the seminiferous tubules of the testis suffered different levels of damage, but not as serious as that of the G1 group.

4. The Radiation Damage Sustained in Organs at One Month after Treating the Liver Tumor by BNCT The histopathological section did not show any abnormalities in the testis 4 days after the BNCT treatment of liver tumor. But at one month after the BNCT irradiation, the testis showed visible lesions both with the naked eyes and under microscopic in tissue examination. FIG. 5 shows the radiation effect in the testis at one month after the BNCT treatment. The picture shows the atrophy of seminiferous tubules in the testis, and the degree of atrophy was related to the irradiation doses received in the rat, but the interstitial cells were not affected. FIG. 5A shows that the atrophy of testis in the G1 subgroup was much worse than that of the G3 subgroup, as indicated by FIG. 5B. Moreover, FIG. 5 also shows different degrees of damage in the seminiferous tubules of a testis.

Because the collimator used for carrying out the BNCT treatment in rats had relatively larger aperture, the rats' testes were subjected to neutron irradiation as well. The disadvantage could be remedied by using a collimator of adequate aperture in human clinical trials, as a human body is relatively larger, and the testis is further away from the liver, thus the dose received in the testis will be much smaller.

The present invention has proposed using boric acid as a boron drug in the BNCT for treating liver cancer, which is simple and effective for treating liver tumors. A rat was firstly injected with boric acid and then subjected to neutron irradiation. On the $10^{th}$ day after BNCT treatment, the rats that received different irradiation doses had shown visible reductions in tumor size as observed in ultrasound imaging, and the distribution of blood vessels growing in tumor, as well as the surrounding thereon was also clearly reduced. On the $30^{th}$ day after BNCT treatment, the tumor size was reduced by approximately 90%, and the histopathological section of the fibrotic lumps showed that no tumor cells were present therein. At 80 days after the BNCT irradiation, the animals were sacrificed and liver surfaces thereof were observed, which showed no presence of tumors. Only the rats that received 11.18 Gy of irradiation dose showed clear testicular atrophy. The present has shown that using boric acid as a boron drug in BNCT is effective for treating liver cancer.

What is claimed is:

1. A Boron Neutron Capture Therapy (BNCT) method for treating a liver cancer in a subject comprising administering boric acid to said subject, and subjecting said liver cancer in the subject to neutron irradiation from a source that emits epithermal neutrons, wherein said boric acid is in the form of an aqueous solution, wherein said administering comprises intravenously injecting said aqueous solution of boric acid to said subject, and wherein said method does not comprise administering any drug other than boric acid to said subject.

2. The BNCT method of claim 1 wherein boron of said boric acid is composed of a majority of $^{10}B$ stable isotope.

3. The BNCT method of claim 2 wherein said boron of said boric acid is composed of about 99% of $^{10}B$ stable isotope.

4. The BNCT method of claim 1 wherein said subject is human.

5. The BNCT method of claim 4 wherein said administering comprises intravenously injecting said aqueous solution of boric acid to said human in a dose of about 5-60 mg of $^{10}B$ stable isotope per kilogram of human body weight.

6. The BNCT method of claim 5 further comprising measuring a concentration of $^{10}B$ stable isotope in the subject's blood, wherein said neutron irradiation is carried out when the concentration measured is more than 20 μg $^{10}B$ stable isotope/mL.

7. The BNCT method of claim 1 wherein said liver cancer in the subject is started to be subjected to the neutron irradiation within a period of 10-120 minutes immediately following the intravenous injection.

8. The BNCT method of claim 1 wherein said liver cancer in the subject is started to be subjected to the neutron irradiation within a period of 30-80 minutes immediately following the intravenous injection.

9. The BNCT method of claim 1 wherein said neutron irradiation is carried out with a physical dose of 5-12 Gy.

10. The BNCT method of claim 1 wherein said neutron irradiation is carried out with a physical dose of 7-10 Gy.

11. The method of claim 1 wherein the epithermal neutrons have energies between about 0.5 eV and about 10 keV.

12. A method of using boric acid in treating a liver cancer in a patient by BNCT comprising preparing an aqueous solution of boric acid, wherein boron of said boric acid is composed of a majority of $^{10}B$ stable isotope; intravenously injecting said aqueous solution of boric acid to said patient in a dose of about 5-60 mg of $^{10}B$ stable isotope per kilogram of patient body weight; and conducting neutron irradiation from a source that emits epithermal neutrons to said patient within a period of 10-120 minutes after said intravenous injection, and wherein said method does not comprise administering any drug other than boric acid to said subject.

13. The method of claim 12 wherein said period is 30-80 minutes.

14. The method of claim 12 wherein the epithermal neutrons have energies between about 0.5 eV and about 10 keV.

15. A method of using boric acid in treating a liver cancer in a patient by BNCT comprising preparing an aqueous solution of boric acid, wherein boron of said boric acid is composed of a majority of $^{10}B$ stable isotope; intravenously injecting said aqueous solution of boric acid to said patient in a dose of about 5-60 mg of said $^{10}B$ stable isotope per kilogram of patient body weight; monitoring a concentration of said $^{10}B$ stable isotope in the patients blood; and conducting neutron irradiation from a source that emits epithermal neutrons to said patient according to a result of said monitoring, wherein said monitoring comprises measuring concentrations of said $^{10}B$ stable isotope in the patient's blood and comparing the measured concentrations to a desired value wherein said desired value is more than 20 μg of said $^{10}B$ stable isotope/mL, and wherein said method does not comprise administering any drug other than boric acid to said subject.

16. The method of claim 15 wherein the epithermal neutrons have energies between about 0.5 eV and about 10 keV.

* * * * *